(12) United States Patent
Oikawa

(10) Patent No.: US 6,587,539 B2
(45) Date of Patent: Jul. 1, 2003

(54) RADIOGRAPHIC APPARATUS

(75) Inventor: Shiro Oikawa, Shiga-ken (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 10/068,891

(22) Filed: Feb. 11, 2002

(65) Prior Publication Data

US 2002/0131549 A1 Sep. 19, 2002

(30) Foreign Application Priority Data

Mar. 13, 2001 (JP) .......................................... 2001-070720

(51) Int. Cl.$^7$ ............................ G01N 23/00; A61B 6/00
(52) U.S. Cl. ........................... 378/19; 378/4; 382/128
(58) Field of Search .............................. 378/19, 4, 15, 378/62, 98.8, 98.6; 382/128

(56) References Cited

U.S. PATENT DOCUMENTS 5,590,164 A * 12/1996 Kawai et al. .................. 378/4
5,838,756 A * 11/1998 Taguchu et al. ............... 378/4

* cited by examiner

Primary Examiner—Drew A. Dunn
Assistant Examiner—Irakli Kiknadze
(74) Attorney, Agent, or Firm—Rader, Fishman & Grauer PLLC

(57) ABSTRACT

An X-ray tube and an X-ray area detector are driven synchronously in scanning action to revolve about a scan axis extending substantially through the center of a region of interest of an object under examination. An image processor performs a predetermined image processing on projection data detected in each scan position. In the image processing, a low-pass filtering is applied to projection data in each row of pixels of the area detector perpendicular to a direction corresponding to the scan axis, the low-pass filtering being in accordance with a location on the scan axis to which each row of pixels is projected. This filtering reduces artifacts due to a volume scan mode appearing in three-dimensional volume data of the region of interest generated by projecting the projection data after the low-pass filtering back to a virtual three-dimensional lattice.

16 Claims, 14 Drawing Sheets

RADIOGRAPHIC APPARATUS

BACKGROUND OF THE INVENTION (1) Field of the Invention

This invention relates to radiographic apparatus used in medical, industrial and other fields for producing sectional images of patients or objects under examination. More particularly, the invention relates to a technique for reducing artifacts appearing in the sectional images.

(2) Description of the Related Art

Conventional radiographic apparatus include a CT (Computed Tomography) type X-ray radiographic apparatus (hereinafter called X-ray CT apparatus where appropriate), for example, which has made remarkable progress in recent years. This X-ray CT apparatus has an X-ray tube and an image intensifier opposed to each other across an object under examination. The X-ray tube emits X rays in the form of a cone beam to the object, and the image intensifier two-dimensionally detects X rays transmitted through the object. Radiography is performed while synchronously driving the X-ray tube and image intensifier to make one revolution (at least a half revolution) in a single plane about a scan axis set substantially centrally of a region of interest of the object and extending perpendicular to that plane. This operation acquires transmitted images for one revolution (at least a half revolution) about the body axis of the object.

This X-ray CT apparatus carries out an image reconstruction, by using the Feldkamp method, from the plurality of transmitted images acquired, to produce three-dimensional volume data of the region of interest of the object. When a sectional plane is selected from this three-dimensional volume data, the selected sectional image (sectional image seen in a direction along the body axis of the object) is displayed on a monitor or the like.

In this way, three-dimensional volume data of the region of interest is obtained in one radiographic operation. This provides an advantage that an image of a desired sectional plane may be displayed quickly after the radiographic operation, simply by selecting the sectional plane.

However, the conventional apparatus noted above has the following drawback. With the image reconstruction using the Feldkamp method, artifacts appear in a reconstructed image of a position in the more pronounced way, the farther away along the scan axis that position is from a center plane located substantially centrally of the region of interest of the object and extending perpendicular to the scan axis. This is believed due to a volume scan mode as described below.

As noted above, the X-ray tube emits X rays in the form of a cone beam to the object, and the image intensifier two-dimensionally detects X rays transmitted through the object. An image reconstruction is carried out, by using the Feldkamp method, based on transmitted images detected in varied scan positions. For example, point-to-point paths extending between the center of cone beam X rays emitted from the X-ray tube and a pixel located on the detecting plane of the image intensifier substantially centrally along the scan axis are in the same slice plane, that is the point-to-point paths are in agreement, for different scan positions. Thus, a reconstructed sectional image of a substantially center plane of a three-dimensional volume is free from artifacts due to a disagreement of point-to-point paths. However, point-to-point paths extending between the center of cone beam X rays emitted from the X-ray tube and a pixel located on the detecting plane of the image intensifier away from the center along the scan axis, i.e. in a direction of divergence (direction of inclination) of the cone beam X rays, are not in the same slice plane, but are different for different scan positions. Thus, artifacts due to a disagreement among the point-to-point paths appear in a reconstructed image of a position in the more pronounced way, the farther away that position is from the center plane of the three-dimensional volume.

SUMMARY OF THE INVENTION

This invention has been made having regard to the state of the art noted above, and its object is to provide a radio-graphic apparatus that suppresses artifacts and the like due to the volume scan mode.

The above object is fulfilled, according to this invention, by a radiographic apparatus for obtaining sectional images from three-dimensional volume data of a region of interest of an object under examination generated by an image reconstruction of projection data acquired by radiographing the object from varied scan positions, the apparatus comprising:

a radiation source for irradiating the object with penetrating electromagnetic waves in form of a divergent beam;

an area detector opposed to the radiation source across the object for detecting electromagnetic waves transmitted through the object;

a scanning device for causing the radiation source and the area detector synchronously to revolve in an identical plane about a scan axis set substantially centrally of the region of interest;

an image processor for performing a predetermined image processing on projection data detected in the varied scan positions; and a back projection unit for performing the image reconstruction to generate three-dimensional volume data of the region of interest by projecting the projection data processed by the image processor back to predetermined lattice points of a three-dimensional lattice virtually set to the region of interest of the object radiographed;

the image processor applying a low-pass filtering to projection data in each row of pixels of the area detector perpendicular to a direction corresponding to the scan axis, the low-pass filtering being in accordance with a location on the scan axis to which each row of pixels is projected.

With this apparatus, the scanning device causes the radiation source for irradiating the object with penetrating electromagnetic waves in form of a divergent beam and the area detector opposed to the radiation source across the object for detecting electromagnetic waves transmitted through the object, synchronously to revolve in an identical plane about a scan axis set substantially centrally of the region of interest. The image processor applies a low-pass filtering to projection data in each row of pixels of the area detector perpendicular to a direction corresponding to the scan axis, the low-pass filtering being in accordance with a location on the scan axis to which each row of pixels is projected. The back projection unit performs an image reconstruction to generate three-dimensional volume data of the region of interest by projecting the projection data processed by the image processor back to predetermined lattice points of a three-dimensional dimensional lattice virtually set to the region of interest of the object radiographed. In this way, an appropriate low-pass filter is applied to reduce artifacts that would appear in a position in the more pronounced way, the farther away along the scan axis that position is from a center plane located substantially centrally of the region of interest of the object and extending perpendicular to the scan axis. Thus, artifacts are suppressed from appearing in positions of a reconstructed image remote along the scan axis.

Preferably, the image processor is arranged to apply a low-pass filtering to pass the lower frequency for projection data in a row of pixels of the area detector the farther away from an emission reference line extending perpendicular to the scan axis from a beam center of the radiation source. In this way, an appropriate low-pass filter is applied to reduce artifacts that would appear in a position in the more pronounced way, the farther away along the scan axis that position is from a center plane located substantially centrally of the region of interest of the object and extending perpendicular to the scan axis. Thus, artifacts are suppressed from appearing in positions of a reconstructed image remote along the scan axis.

Preferably, the image processor is arranged to apply a low-pass filtering as a diffusion proportional to sin(α), where α is an angle of divergence formed between an emission reference line extending perpendicular to the scan axis from a beam center of the radiation source and a projection line extending from the radiation source and each row of pixels of the area detector. In this way, an appropriate low-pass filter is applied to reduce artifacts that would appear in a position in the more pronounced way, the farther away along the scan axis that position is from a center plane located substantially centrally of the region of interest of the object and extending perpendicular to the scan axis. Thus, artifacts are suppressed from appearing in positions of a reconstructed image remote along the scan axis.

Preferably, the area detector is a flat panel detector with gate lines arranged in a direction corresponding to a direction of the scan axis, the image processor applying the low-pass filtering by simultaneously turning on gates of a predetermined number of rows of pixels corresponding to the direction of the scan axis. In this way, an appropriate low-pass filter is applied to reduce artifacts that would appear in a position in the more pronounced way, the farther away along the scan axis that position is from a center plane located substantially centrally of the region of interest of the object and extending perpendicular to the scan axis. Thus, artifacts are suppressed from appearing in positions of a reconstructed image remote along the scan axis.

Preferably, the scanning device performs, instead of the scanning by revolution in the identical plane, a linear scanning for linearly moving one of the radiation source and the area detector in a first direction perpendicular to the scan axis, and the other synchronously therewith in a second direction parallel and counter to the first direction. Thus, also in a non-CT type radiography (in which the radiation source and area detector are not caused to make more than a half revolution about the body axis of the object) which causes the radiation source and area detector to move linearly, parallel to each other, and scan the object lying in between, and carries out an image reconstruction to generate three-dimensional volume data of a region of interest of the object, artifacts are suppressed from being reconstructed in positions having varied angles of divergence.

Preferably, two arcuate tracks are set on a circumferential track around the object to be opposed to each other across the object such that a straight line between midpoints of the two arcuate tracks coincides with the scan axis, the scanning device performing, instead of the scanning by revolution in the identical plane, an arcuate scanning for moving the radiation source on one of the arcuate tracks, and the area detector on the other arcuate track synchronously therewith to maintain a fixed distance from the radiation source. Thus, also in a non-CT type radiography which causes the radiation source and area detector to move separately and arcuately and scan the object lying in between, and carries out an image reconstruction to generate three-dimensional volume data of a region of interest of the object, artifacts are suppressed from being reconstructed in positions having varied angles of divergence.

Preferably, the scanning device performs, instead of the scanning by revolution in the identical plane, a circular scanning for revolving the radiation source in one of parallel planes opposed to each other across the object and extending perpendicular to the scan axis, and the area detector in the other plane synchronously therewith and in a direction opposite to a direction of revolution of the radiation source. Thus, also in a non-CT type radiography which causes the radiation source and area detector to revolve separately in the two parallel planes and scan the object lying in between, and carries out an image reconstruction to generate three-dimensional volume data of a region of interest of the object, artifacts are suppressed from being reconstructed in positions having varied angles of divergence.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

DESCRIPTION OF THE PREFERRED EMBODIMENTS

Preferred embodiments of this invention will be described in detail hereinafter with reference to the drawings.

Figure 1:
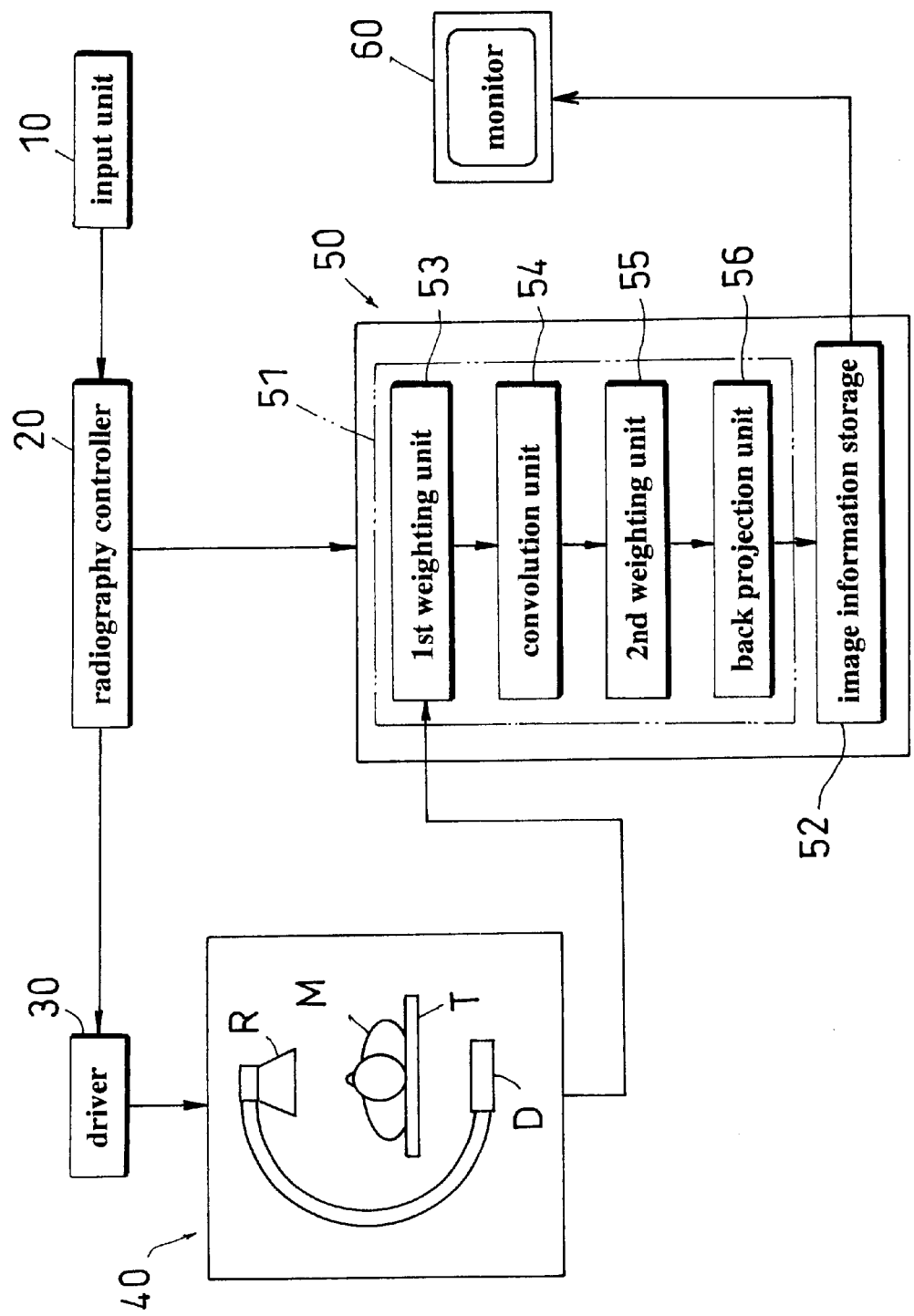
FIG. 1 is a block diagram of an X-ray CT apparatus according to this invention.

A CT-type X-ray radiographic apparatus (hereafter called X-ray CT apparatus where appropriate) will be described as one example of radiographic apparatus according to the invention. FIG. 1 is a block diagram of the X-ray CT apparatus.

This X-ray CT apparatus includes an input unit 10 for inputting various information and instructions, a radiography controller 20 for controlling X-ray radiography based on the information and instructions inputted, a driver 30 for operating an image pickup station 40 under control of the radiography controller 20, the image pickup station 40 for picking up images of a region of interest of a patient M, a data processor 50 for performing an image reconstruction to generate three-dimensional volume data of the region of interest of patient M from image information provided by the image pickup station 40, and storing the three-dimensional volume data generated, and a monitor 60 for displaying image information stored in the data processor 50.

Figure 2A:
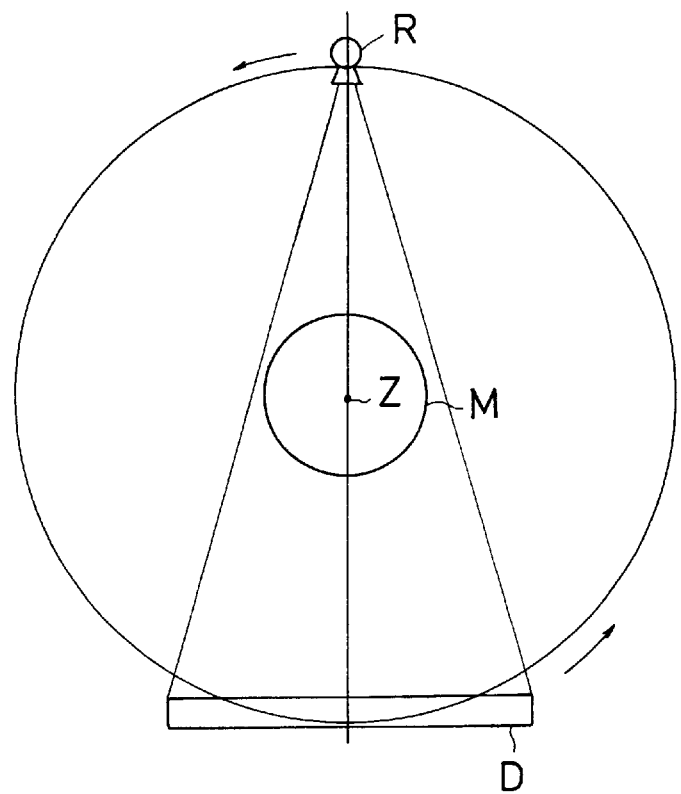
FIG. 2A is a schematic plan view showing one scan mode of an X-ray tube and a flat panel X-ray detector in the X-ray CT apparatus.
Figure 2B:
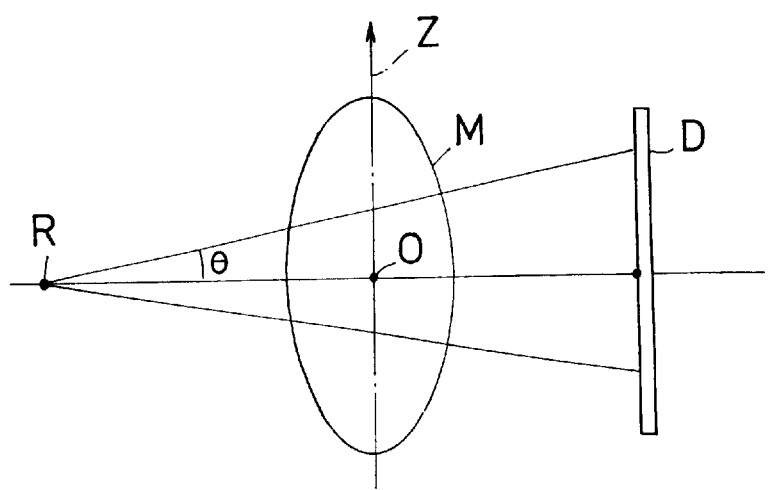
FIG. 2B is a schematic side view of the X-ray tube and flat panel X-ray detector shown in FIG. 2A.

The construction and function of each of these components will be described hereinafter. FIG. 2A is a schematic plan view showing one scan mode of an X-ray tube R and a flat panel X-ray detector D in the X-ray CT apparatus. FIG. 2B is a schematic side view of the X-ray tube R and flat panel X-ray detector D shown in FIG. 2A. As shown in FIG. 2A, the X-ray tube R and flat panel X-ray detector D are opposed to each other across the patient M. Radiography is performed while synchronously driving the X-ray tube R and flat panel X-ray detector D to make one revolution (at least a half revolution) in the same plane about a scan axis Z set substantially centrally of the region of interest of patient M, thereby to acquire transmitted images for one revolution (at least a half revolution) about the body axis of patient M. Before picking up images of the region of interest of patient M, the input unit 10 is operated to input and determine a distance from the X-ray tube R to the flat panel X-ray detector D, and intervals of circular movement of the X-ray tube R and flat panel X-ray detector D. Input devices such as a keyboard, mouse and/or touch panel are used as the input unit 10. The above X-ray tube R corresponds to the radiation source in this invention.

The input unit 10, driver 30 and data processor 50 are connected to the radiography controller 20. The radiography controller 20 controls the driver 30 and data processor 50 based on information inputted from the input unit 10. The contents of control will be described hereinafter in relation to each controlled component.

As shown in FIG. 2A, the driver 30 synchronously drives the X-ray tube R and flat panel X-ray detector D opposed to each other across the patient M, to make one revolution (at least a half revolution) in the same plane about the scan axis Z set substantially centrally of the region of interest of patient M. At this time, as shown in FIG. 2B, the X-ray tube R and flat panel X-ray detector D are opposed to each other, such that the center point of X rays emitted in the form of a cone beam from the X-ray tube R toward the patient M always passes through the center point 0 of a particular sectional plane of the patient M which is a particular point on the scan axis Z, and impinges on the center point of the detecting plane of flat panel X-ray detector D in a direction perpendicular thereto. The above driver 30 corresponds to the scanning device in this invention.

As shown in FIG. 1, the image pickup station 40 includes a top board T for supporting the patient M, the X-ray tube R for emitting X rays in the form of a cone beam toward the patient M, and the flat panel X-ray detector D for detecting X rays transmitted through the patient M.

Figure 3:
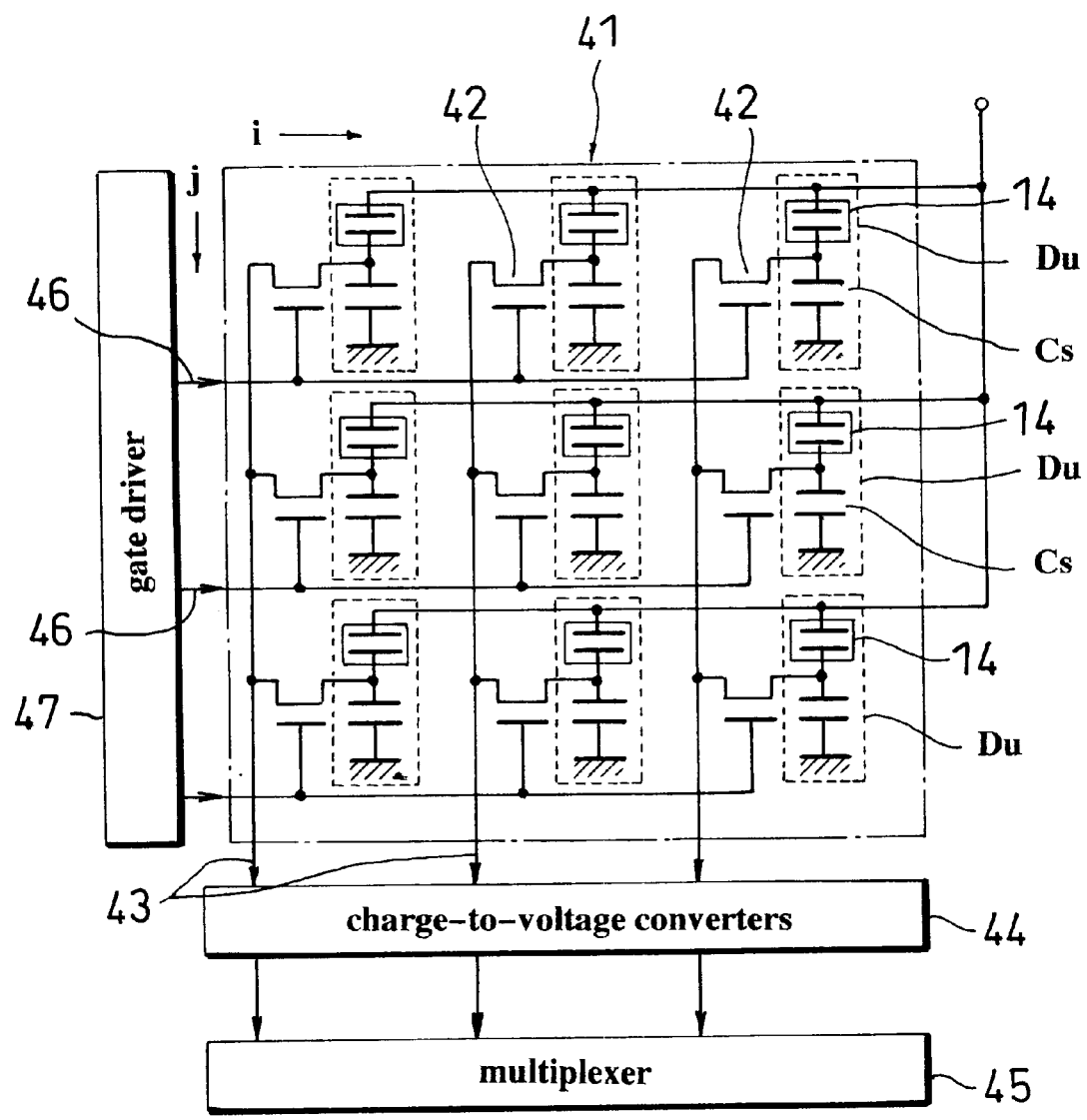
FIG. 3 is a view showing a construction of the flat panel X-ray detector.

The flat panel X-ray detector D is the type that detects fluoroscopic images of the patient M produced by the X-ray emission from the X-ray tube R, and converts the image data into electric signals for output as X-ray detection signals. As shown in FIG. 3, the X-ray detector D is in the form of a two-dimensional matrix with numerous detecting elements Du arranged in a crisscross pattern. The detecting elements Du of the flat panel X-ray detector D in this embodiment are arranged in a square matrix, e.g. 1,024 arranged horizontally (i-rows) and 1,024 arranged vertically j-columns). For expediency of description, the square matrix is assumed here to have 1,000 detecting elements Du arranged horizontally and 1,000 detecting elements Du arranged vertically. FIG. 3 shows a matrix arrangement of only nine elements Du, i.e. 3 horizontally and 3 vertically. As distinct from an image intensifier which must have a circular detecting plane, the flat panel X-ray detector D having a rectangular plane is useful in that it may have a square detecting plane suitable for detecting images of large sites such as the chest and abdomen.

Figure 4:
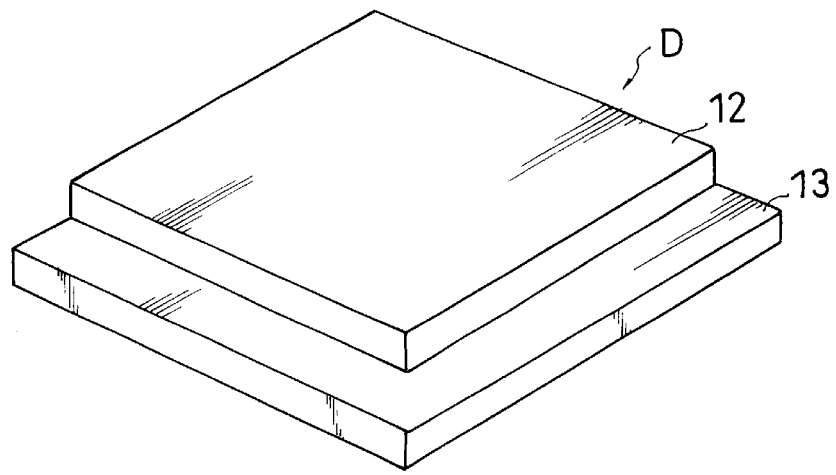
FIG. 4 is a perspective view showing an outline of the flat panel X-ray detector.

As shown in FIG. 4, the flat panel X-ray detector D has a laminated structure, and includes an X-ray converting layer 12 for converting incident X rays into electric charge or light, and a detecting array layer 13 having a matrix arrangement of elements for detecting the charge or light generated by the X-ray converting layer 12. The plane size of X-ray converting layer 12 of this flat panel X-ray detector D may be 30 cm by 30 cm, for example.

Figure 5A:
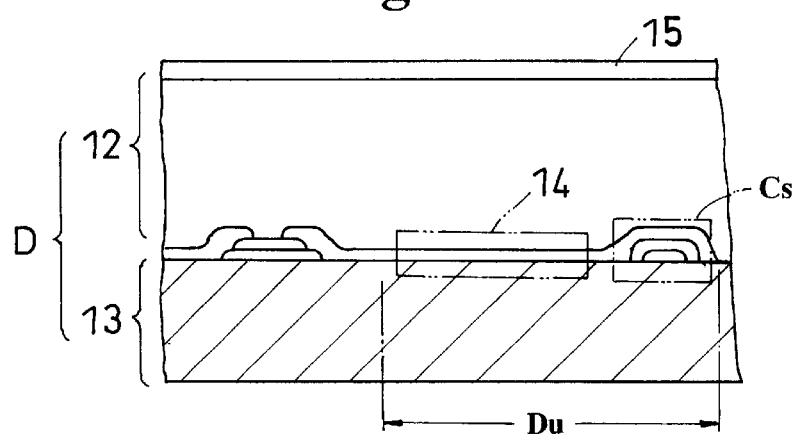
FIGS. 5A and 5B are sectional views showing a layer structure of the flat panel X-ray detector.
Figure 5B:
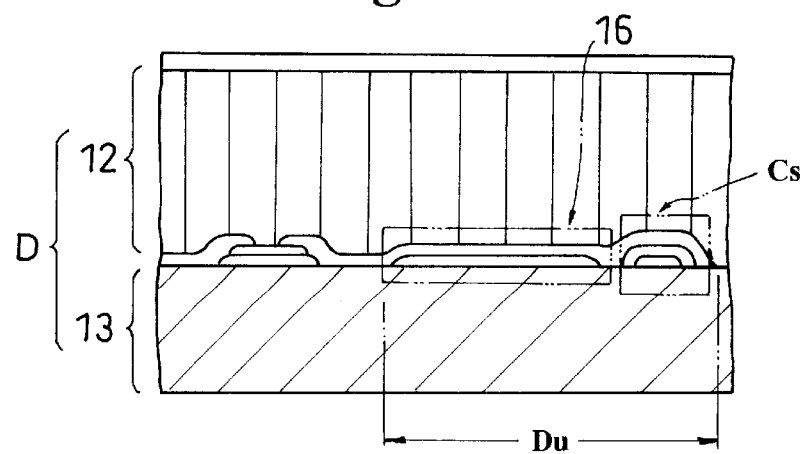

The flat panel X-ray detector D may be the direct conversion type shown in FIG. 5A or the indirect conversion type shown in FIG. 5B. In the former, direct conversion type, the X-ray converter layer 12 consists of a selenium layer, CdZnTe layer or the like for converting incident X rays directly into electric charges. The detecting array layer 13 has charge collecting electrodes formed on the surface thereof and opposed to a surface electrode 15 to act as charge detecting elements 14 for detecting the charges, and capacitors Cs for storing the charges. Each charge detecting element 14 and a part of X-ray conversion layer 12 thereover constitute one detecting element Du. In the latter, indirect conversion type, the X-ray converting layer 12 consists of a scintillator layer for converting incident X rays into light. The detecting array layer 13 has photodiodes formed on the surface thereof to act as photo detecting elements 16 for detecting the light, and capacitors Cs for storing electric charges. Each photo detecting element 16 and a part of X-ray conversion layer 12 thereover constitute one detecting element Du.

As shown in FIG. 3, the flat panel X-ray detector D includes an X-ray detector substrate 41 with the X-ray converting layer 12 and detecting array layer 13 formed thereon, the capacitors Cs for storing collected carriers (collected charges) from the carrier collecting electrodes (charge collecting electrodes) on the X-ray detector substrate 41, thin film transistors (TFT) acting as charge fetching switching elements 42, which are normally turned off, for fetching the charges stored in the capacitors Cs, and a multiplexer 45 and a gate driver 47 acting as reading circuits for i- and j-directions.

As shown in FIG. 3, the flat panel X-ray detector D has the thin film transistors acting as the switching elements 42 of detecting elements Du. The thin film transistors have sources thereof connected to vertical sense lines 43 arranged in i-direction, and gates connected to horizontal sense lines 46 arranged in j-direction. The sense lines 43 are connected to the multiplexer 45 through a group of charge-to-voltage converters (group of preamplifiers) 44. The sense lines 46 are connected to the gate driver 47. In the group of charge-to-voltage converters 44, though not shown, one charge-to-voltage converter is connected to each sense line 43.

In the flat panel X-ray detector D, scan signals are inputted to the multiplexer 45 and gate driver 47 for fetching signals. The detecting elements Du are identified by means of addresses (0 to 999 since the number of detecting elements Du is 1,000; 0 to 1023 where 1024 detecting elements Du are provided) sequentially allocated to the detecting elements Du along the i- and j-directions. Thus, the fetching scan signals serve as signals designating the addresses in the i-direction or j-direction.

In response to scan signals for the j-direction, the gate driver 47 applies a fetching voltage to the sense lines 46 arranged in the j-direction, whereby detecting elements Du are selected on a column-by-column basis. When the multiplexer 45 is switched by scan signals for the i-direction, the charges stored in the capacitors Ca of the detecting elements Du in the selected columns are successively outputted through the charge-to-voltage converter group 44 and multiplexer 45. Thus, the flat panel X-ray detector D successively outputs detection signals to the data processor 50 in real time. The above flat panel X-ray detector D corresponds to the area detector in this invention.

The construction and functions of data processor 50 will be described next. As shown in FIG. 1, the data processor 50 includes an image processor 51 for performing an image reconstruction (which is based on the Feldkamp method) to generate three-dimensional volume data of the region of interest from projection data (detection signals) detected in varied scan positions at the image pickup station 40, and an image information storage 52 for storing the three-dimensional volume data of the region of interest generated by the image processor 51. Specific functions of the image processor 51 and image information storage 52 will be described hereinafter.

A series of processing steps for the image reconstruction based on the Feldkamp method to generate the three-dimensional volume data of the region of interest will be outlined with reference to FIGS. 1 and 2. As shown in FIG. 2, the X-ray tube R and flat panel X-ray detector D opposed to each other across the patient M are synchronously driven to make one revolution about the scan axis Z set substantially centrally of the region of interest of patient M, thereby to scan the patient M and pick up images thereof. This operation acquires a group of projection data of the region of interest of patient M detected in varied scan positions. Next, the projection data are individually subjected to a first weighting process described hereinafter. Then, a predetermined convolution process described hereinafter is performed on the projection data resulting from the first weighting process. Next, a second weighting process described hereinafter is performed on the projection data resulting from the convolution process. Next, the projection data resulting from the second weighting process are individually subjected to a predetermined back projection (BP) to be described hereinafter, to generate a BP image (three-dimensional volume data). In this way, an image reconstruction is carried out to generate three-dimensional volume data of the region of interest. The operator may observe an image of any sectional plane (seen in the direction of the scan axis (Z-axis)) selected from the three-dimensional volume data.

As shown in FIG. 1, the image processor 51 includes a first weighting unit 53 for performing the first weighting process individually on the group of projection data acquired by radiography, a convolution unit 54 for performing the predetermined convolution process on each projection data after the first weighting process, a second weighting unit 55 for performing the second weighting process on each projection data after the convolution process, and a back projection unit 56 for performing the predetermined back projection (BP) individually of the projection data after the second weighting process to generate a BP image (three-dimensional volume data).

Figure 6:
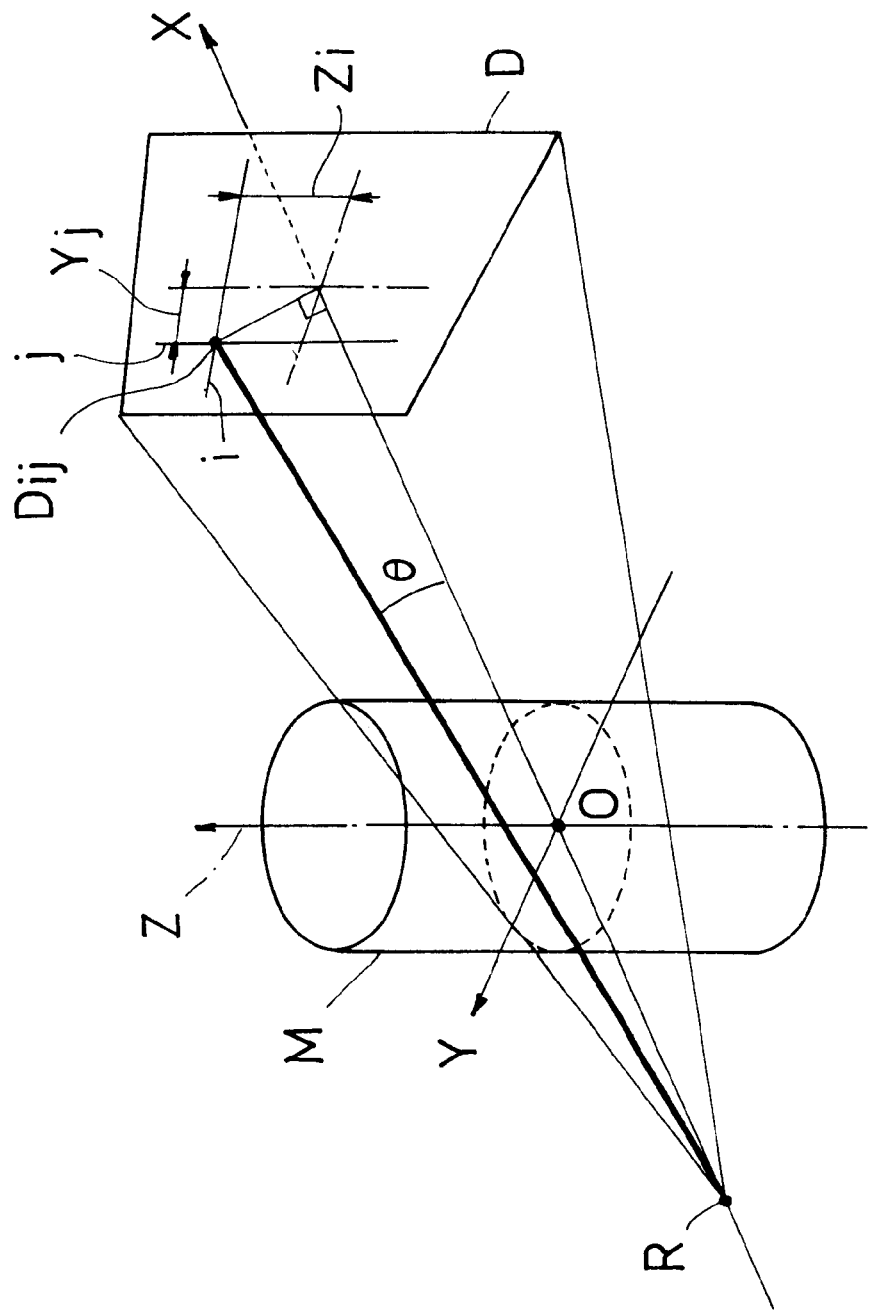
FIG. 6 is a schematic view illustrating a cosine correction by a first weighting unit in the CT apparatus.

The first weighting unit 53 performs the first weighting process (ring correction and cosine correction) individually on the group of projection data acquired by radiography. Specifically, as shown in FIG. 6, what is known as a ring correction is carried out to correct pixel detection level fluctuations in the viewing direction, one pixel row i after another of the flat panel X-ray detector D, for projection data detected in varied scan positions by the flat panel X-ray detector D. As shown in FIG. 6, the center point of X rays emitted in the form of a cone beam from the X-ray tube R toward the patient M always passes through the center point O of a particular sectional plane of patient M (which is also a point on the scan axis Z), and impinges on the center point of the detecting plane of flat panel X-ray detector D in a direction perpendicular thereto.

Then, as shown in FIG. 6, the first weighting unit 53 performs, on the projection data after the ring correction, a sine correction based on the following equation (1):

$$\cos \theta = RD/(RD^2 + Yj^2 + Zj^2)^{1/2} \quad (1)$$

where RD is a distance from the X-ray tube R to the flat panel X-ray detector D.

Figure 7:
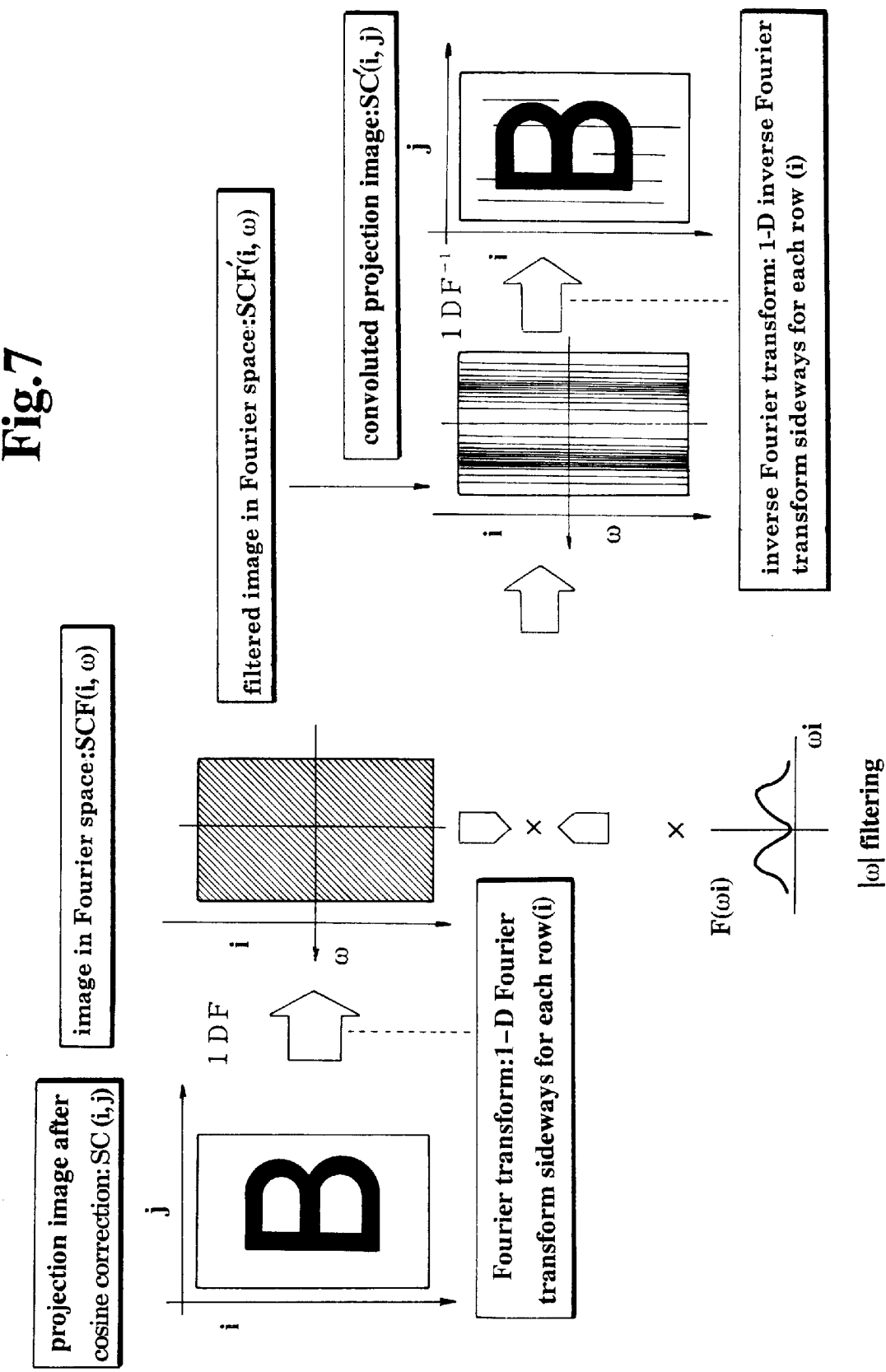
FIG. 7 is a schematic view illustrating a series of processing steps executed by a convolution unit in the CT apparatus.

That is, the cosine correction is performed by multiplying each pixel by $\cos \theta$ of equation (1). For example, a cosine-corrected value of pixel Dij is derived from $Yj \cdot \cos \theta$. This is fixed regardless of the views, and therefore is provided as a cosine correction table in advance. In this way, projection data after the cosine correction is calculated (FIG. 7 shows this as "projection image after cosine correction: SC (i,j)").

The convolution unit 54 performs the predetermined convolution process on each projection data after the first weighting process, i.e. the projection image after cosine correction: SC (i, j). The convolution process performed in the real space is equivalent to a filtering process in the Fourier space. Thus, for expediency of description, the above predetermined convolution process will be described as filtering processes performed in the Fourier space ($|\omega|$ filtering (absolute value omega) filtering process and a low-pass filtering process shown in FIG. 7). The $|\omega|$ filtering process performed by the convolution unit 54 will be described first, and then the low-pass filtering process by the convolution unit 54 will be described.

The $|\omega|$ filtering process performed by the convolution unit 54 will be described first. The convolution unit 54 includes a one-dimensional Fourier transform unit for performing a one-dimensional Fourier transform sideways on each i-row of flat panel X-ray detector D to generate an image in Fourier space SCF (i, ω), an |ω| filtering unit for applying an |ω| filter to the image in Fourier space SCF (i, ω) resulting from the one-dimensional Fourier transform, and a one-dimensional inverse Fourier transform unit for performing a one-dimensional inverse Fourier transform of the image in Fourier space SCF' (i, ω) |ω|-filtered by the |ω| filtering unit to put the image back to real space data.

As shown in FIG. 7, the filtering unit includes an |ω| filtering unit having a filter for suppressing high frequency noise by isotropically reducing the high frequency regions in the i-direction of the image in Fourier space SCF (i, ω) resulting from the one-dimensional Fourier transform, and a filter dependent on a data collection scan mode. The filter dependent on a data collecting scan mode suppresses DC components to reduce artifacts caused by the DC components being emphasized, when the filtered image in Fourier space SCF' (i, ω) is subjected to the one-dimensional inverse Fourier transform.

The meaning of the filtering process performed in the one-dimensional Fourier space will be described now. The filtering process performed in the one-dimensional Fourier space is mathematically expressed by the following equation (2):

$$SCF'(i, \omega) = SCF(i, \omega) \times M(\omega i) \quad (2)$$

where SCF' (i, ω) is the filtered one-dimensional image in Fourier space, and M (ωi) is a function representing filter characteristics of the above filtering unit. M (ωi) is expressed by the following equation (3) as a product of two functions representing the filter characteristics:

$$M(\omega i) = Mi(\omega i) \cdot M\omega(\omega i) \quad (3)$$

A typical example of each filter function system shown in the equation (3) will be described hereinafter.

Figure 8A:
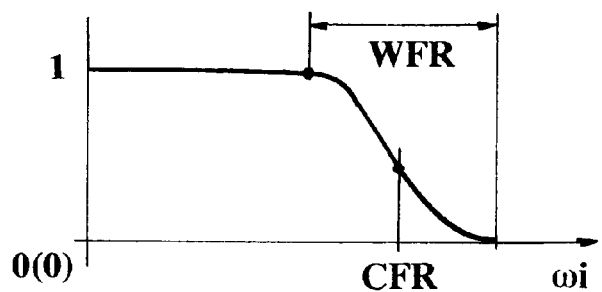
FIGS. 8A and 8B are characteristic views showing filter functions of an $|\omega|$ filtering unit in the CT apparatus.

M (ωi) has a filter characteristic as shown in FIG. 8A, which is expressed by the following equations (4)–(6):

$$Mi(\omega i) = 1 \text{ (where } \omega i < CFR - WFR/2) \quad (4)$$

$$Mi(\omega i) = \{1 - \sin((\omega i - CFR) \cdot \pi / WFR)\}/2$$

$$\text{(where } CFR - WFR/2 < \omega i < CFR + WFR/2) \quad (5)$$

$$Mi(\omega i) = 0 \text{ (where } CFR + WFR/2 < \omega i) \quad (6)$$

However, the function has a sine wave form with high frequency components smoothly attenuating as shown in FIG. 8A. CFR is a cutoff frequency, and WFR is a total transition frequency width of filter strength (see FIG. 8A). This Mi (ωi) deletes high frequency components from the one-dimensional Fourier space.

Figure 8B:
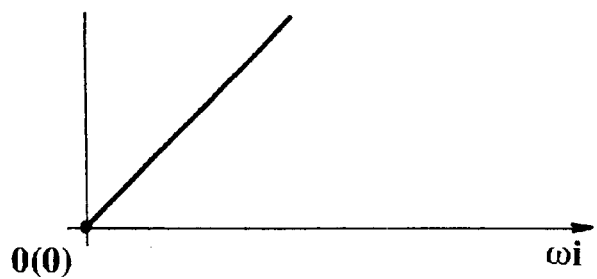

Mω (ωi) has a filter characteristic shown in FIG. 8B, which is expressed by the following equation (7):

$$M\omega(\omega i) = |\omega| \quad (7)$$

FIGS. 8A and 8B show only the characteristics in the plus direction along the horizontal axis. The characteristics in the minus direction along the horizontal axis are omitted since these are in linear symmetry with the characteristics in the plus direction about the vertical axis.

Reverting to FIG. 7, the one-dimensional inverse Fourier transform unit performs a one-dimensional inverse Fourier transform of the image in Fourier space SCF' (i, ω) |ω|-filtered by the |ω| filtering unit to put the image back to real space data and generate a convoluted projection image SC' (i,j).

Next, the low-pass filtering process by the convolution unit 54 will be described. The convolution unit 54 has a Fourier space low-pass filtering unit for applying a low-pass filter to pixels in the i-rows of the projection image SC' (i, j) after the convolution shown in FIG. 7, based on positions on the scan axis (in the Z-direction) to which the pixels in the i-rows are projected. The low-pass filter has a Gaussian low-pass filter characteristic. The necessity of this low-pass filtering will be discussed below.

Figure 10A:
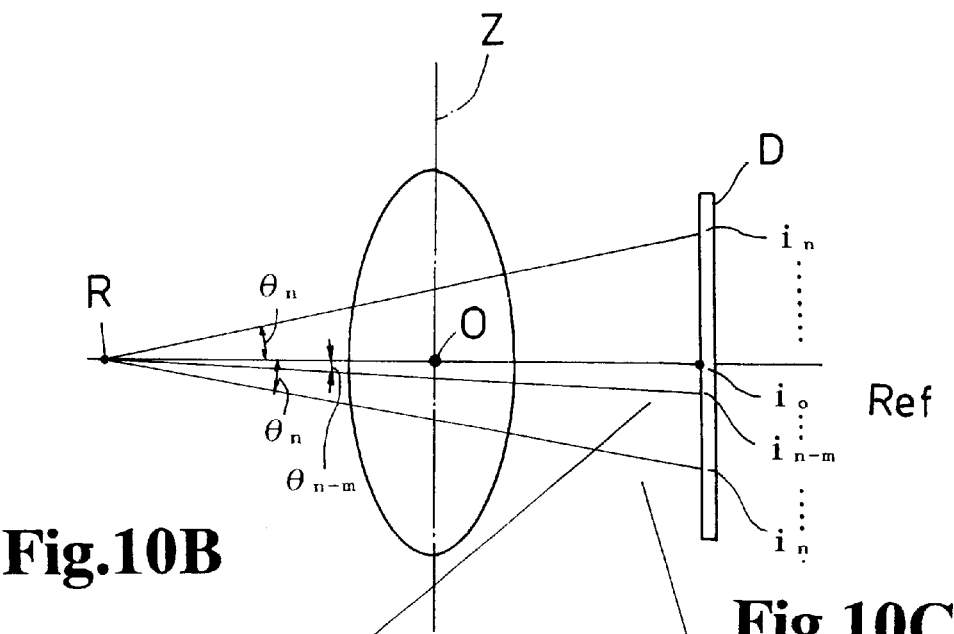
FIGS. 10A through 10C are schematic views illustrating a low-pass filtering applied to each row of pixels according to an angle of divergence.
Figure 10B:
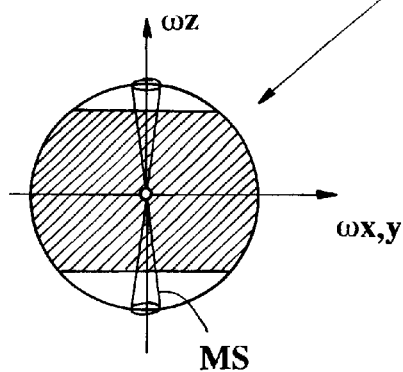
Figure 10C:
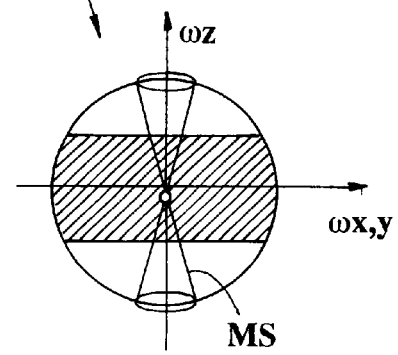

Assume that only the |ω| filtering process shown in FIG. 7 is performed on all the projection data from the varied scan positions, and rows adjacent a row i of pixels in the projection image after the convolution SC' (i, j) are subjected to a back projection (BP) to provide three-dimensional volume data, which is then subjected to a three-dimensional Fourier transform to produce three-dimensional Fourier transform data (three-dimensional Fourier distribution image). The three-dimensional Fourier transform data (three-dimensional Fourier distribution image) in a row of pixels $i_{n-m}$ adjacent the center of flat panel X-ray detector and in a row of pixels in remote from the center, as shown in FIG. 10A, each have two missing cones MS centering on the ωZ-axis, with the vertices thereof meeting at the origin of the Fourier space coordinates, as shown in FIGS. 10B and 10C. The two missing cones MS are void of data. The two missing cones MS are different in size (volume) from one row of pixels i to another of flat panel X-ray detector D. That is, the missing cones MS have a central angle and volume enlarging in proportion to an angle of inclination of a point-to-point path extending between the center of the cone beam X rays emitted from the X-ray tube R and each of pixel rows i arranged in the scan axis (Z-axis) of flat panel X-ray detector D, with respect to a straight line (hereinafter called emission reference line Ref where appropriate) extending from the center point of the cone beam X rays through the center point O of a particular slice of patient M to the row of pixels $i_0$ at the center of flat panel X-ray detector D.

As shown in FIG. 10B, a point-to-point path extending between the X-ray tube R and the row of pixels $i_{n-m}$ adjacent the center of the detecting plane of flat panel X-ray detector D is inclined by $\theta_{n-m}$ with respect to the emission reference line Ref. This angle is relatively small, and the disagreement in point-to-point path among the varied scan positions is small, resulting in the missing cones MS of small central angle and volume. The above m and n are integers, m being smaller than n. As shown in FIG. 10C, a point-to-point path extending between the X-ray tube R and the row of pixels $i_n$ remote from the center of the detecting plane of flat panel X-ray detector D is inclined by $\theta_n$ with respect to the emission reference line Ref. This angle is relatively large, and the disagreement in point-to-point path among the varied scan positions is large, resulting in the missing cones MS of large central angle and volume. Thus, the Fourier space low-pass filtering unit is characterized by applying an appropriate low-pass filter to each row of pixels i to lessen influences of the missing cones MS having the larger volume for the row of pixels farther away from the center of flat panel X-ray detector D as shown in FIGS. 10A through 10C.

Figures 9A, 9B:
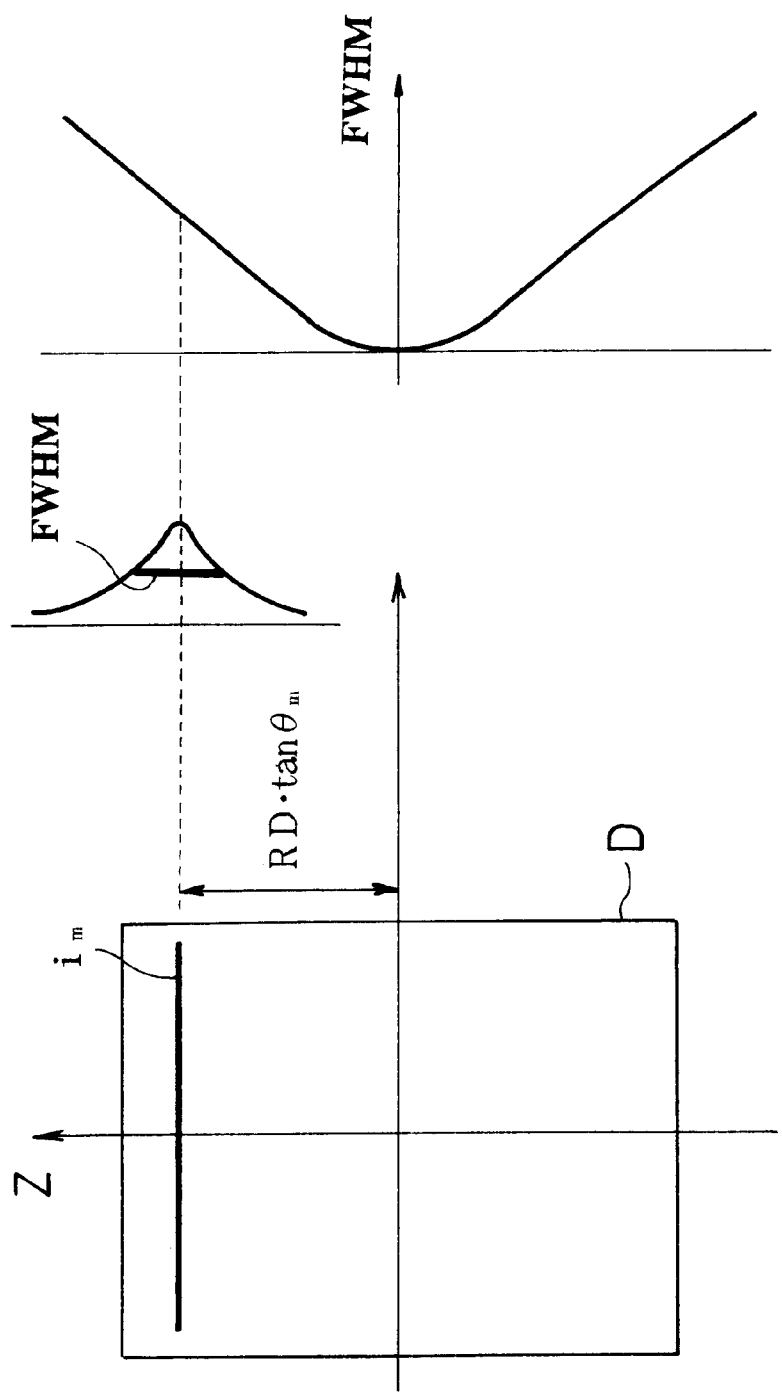
FIGS. 9A and 9B are schematic views illustrating a low-pass filtering applied to each row of pixels according to an angle of divergence.

Specifically, as shown in FIGS. 9 and 10, the Fourier space low-pass filtering unit carries out a low-pass filtering as a diffusion proportional to $\sin(\theta_n)$ on projection data for each pixel row $i_n$, based on an angle of divergence $\alpha(\alpha=\theta_n)$ between the emission reference line Ref and a projection line extending from the X-ray tube R to the row of pixels $i_n$ of flat panel X-ray detector D. As shown in FIG. 9A, for example, a diffusion proportional to $\sin(\theta_n)$ is carried out for the row of pixels $i_m$ of flat panel X-ray detector D. That is, a Gaussian low-pass filter proportional to $\sin(\theta_n)$ is applied to the row of pixel $i_m$ at the distance RD from the X-ray tube R to the flat panel X-ray detector D multiplied by $\tan \theta_m$, i.e. at a distance (=RD·$\tan \theta_m$) from the emission reference line Ref to the row of pixels $i_m$, thereby performing a low-pass filtering at a diffusion level (FWHM: half value width) proportional to $|\sin(\theta_m)|$. FIG. 9B shows characteristics of the diffusion level (FWHM: half value width) proportional to $|\sin(\theta_m)|$. The vertical axis represents the rows of pixels i of flat panel X-ray detector D, and the horizontal axis the diffusion level (FWHM: half value width).

As shown in FIG. 10B, the row of pixels $i_{n-m}$ adjacent the center of the detecting plane of flat panel X-ray detector D has small missing cones that have a small influence, and therefore the diffusion level (FWHM: half value width) is low. That is, only small portions of high frequency components on the $\omega Z$-axis are cut (white portions in FIG. 10B). As shown in FIG. 10C, the row of pixels $i_n$ remote from the center of the detecting plane of flat panel X-ray detector D, has large missing cones that have a strong influence, and therefore the diffusion level (FWHM: half value width) is high. That is, large portions of high frequency components on the $\omega Z$-axis are cut (white portions in FIG. 10C).

In this way, an appropriate low-pass filter is applied to each row of pixels i to reduce the missing cones MS having the larger volume for the row of pixels farther away along the scan axis (Z-axis) from the center of flat panel X-ray detector D. This results in reduced artifacts in the three-dimensional volume data generated by a back projection of the convoluted projection image subsequently performed by the back projection unit 56. The convolution unit 54 described above corresponds to the image processor in this invention.

Figure 11:
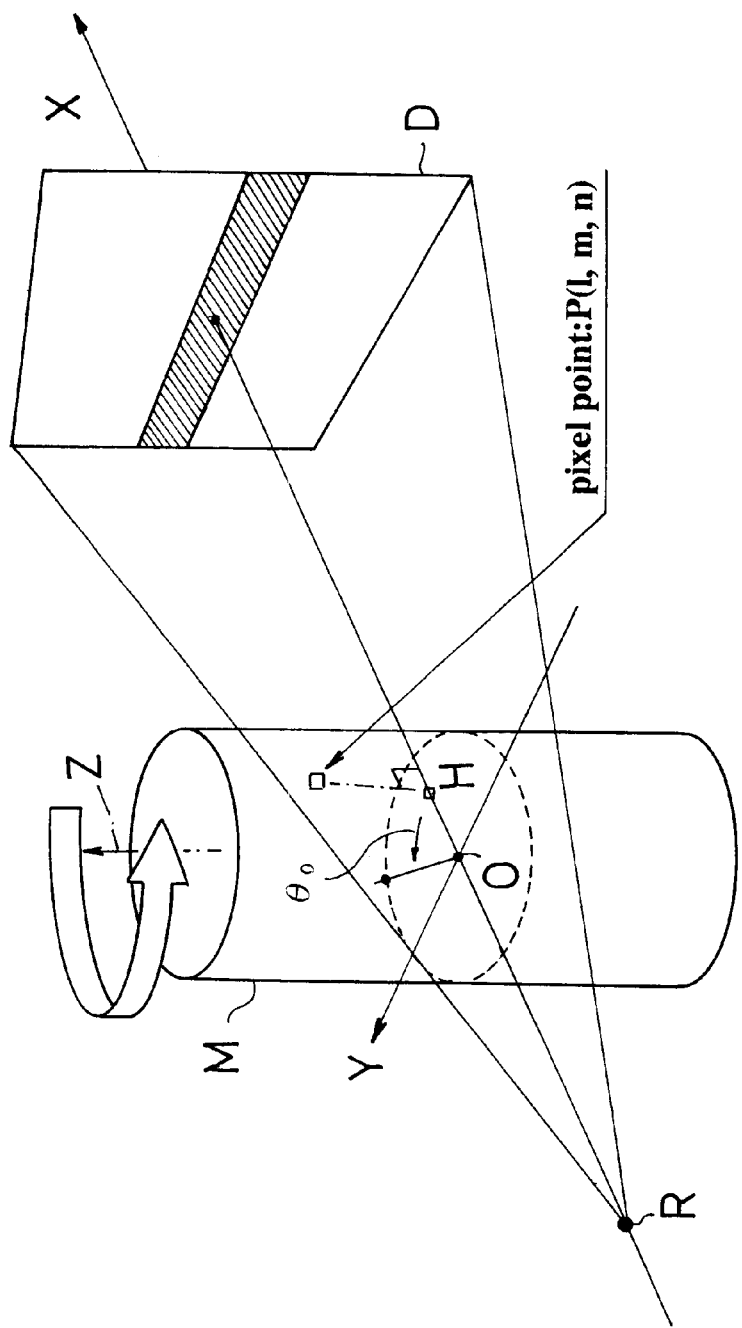
FIG. 11 is a schematic view illustrating convoluted projection data projected back to a virtual three-dimensional lattice.

The second weighting unit 55 performs the second weighting process on the convoluted projection data SC' (i, j) for each scan position. Specifically, a weight function W (l, m, n) for a three-dimensional pixel point: P (l, m, n) in a coordinate system applied to the patient (see FIG. 11) is derived from the following equation (8):

$$W(l, m, n) = RO^2/(RO+OH)^2 \quad (8)$$

where H is a position on the X-axis of a perpendicular extending from the pixel point P (l, m, n).

Figure 12:
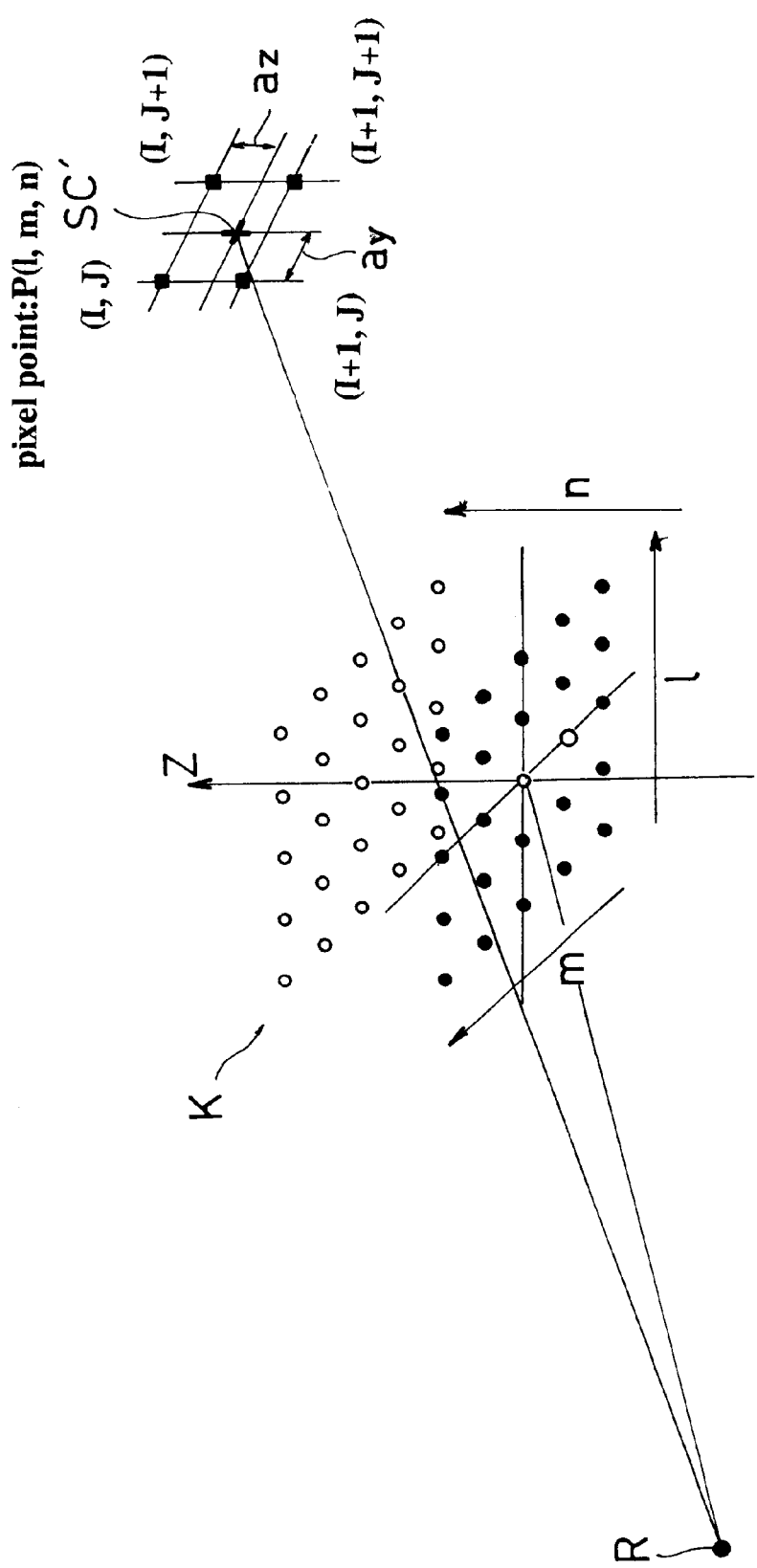
FIG. 12 is a schematic view illustrating convoluted projection data projected back to the virtual three-dimensional lattice.

Then, as shown in FIG. 12, the second weighting unit 55 determines coordinates (I, J) of the projection image SC' (i, j) of the three-dimensional pixel point: P (l, m, n), and weighting mantissa ($a_z$, $a_y$). The second weighting process is carried out as described above.

Next, the back projection unit 56 performs the predetermined back projection (BP) individually of the projection data after the second weighting process to generate a BP image (three-dimensional volume data). Specifically, an image reconstruction is performed to generate three-dimensional volume data of the region of interest of patient M by projecting the group of projection data of the region of interest detected in the varied scan positions and having undergone the second weighting process, back to predetermined lattice points of a three-dimensional lattice K virtually set to the region of interest as shown in FIG. 12. That is, the simple BP image noted hereinbefore is generated. Minimum lattice spacing along the axes of three-dimensional lattice K shown in FIG. 12 is dependent on pixel spacing of flat panel X-ray detector D. That is, the flat panel X-ray detector D has pixels arranged in a two-dimensional matrix of 1,000 by 1,000, and therefore the maximum number of lattice points in each of the directions along the three axes (X-, Y- and Z-axes) of three-dimensional lattice K is 1,000.

Specifically, a computation for linear interpolation and a back projection are carried out according to the following equation (9):

$$I_n(l, m, n) = I_{n-1}(l, m, n) + W(l, m, n) \times \{W_{11} \cdot SC'(I, J) + W_{12} \cdot SC'(I, J+1) + W_{21} \cdot SC'(I+1, J) + W_{22} \cdot SC'(I+1, J+1)\} \quad (9)$$

where $I_n$ (l, m, n) is an accumulation of back projection, and $I_{n-1}$ (l, m, n) is an accumulation of back projection made by preceding steps.

Pixel spacing of the projection image is standardized to 1, and weight functions in a multiplication weighting method as in the following equations (10)–(13) are used:

$$W_{11} = (1-a_z) \cdot (1-a_y) \quad (10)$$

$$W_{12} = (1-a_z) \cdot a_y \quad (11)$$

$$W_{21} = a_z \cdot (1-a_y) \quad (12)$$

$$W_{22} = a_z \cdot a_y \quad (13)$$

A similar back projection is performed on the remaining predetermined lattice points of three-dimensional lattice K. Further, a similar back projection is performed for varied scan positions, i.e. over the range of 380° to generate a BP image (three-dimensional volume data).

The image information storage 52 stores the three-dimensional volume data generated by the back projection unit 56. When the input unit 10 is operated to select image information of any given slice, this image information is outputted to the monitor 60.

The monitor 60 has a function to display selected image information stored in the image information storage 52.

In the above embodiment, the convolution unit 54 applies a low-pass filter to projection data in each row of pixels on the flat panel X-ray detector D perpendicular to the direction corresponding to the scan axis (Z-axis), based on positions on the scan axis (Z-axis) to which the row of pixels is projected. An appropriate low-pass filter is applied to reduce artifacts that would appear in a position in the more pronounced way, the farther away along the scan axis that position is from a center plane located substantially centrally of the region of interest of patient M and extending perpendicular to the scan axis. Thus, artifacts are suppressed from appearing in positions of a reconstructed image remote along the scan axis (Z-axis).

The convolution unit 54 carries out a low-pass filtering on projection data for each row of pixels i of flat panel X-ray detector D as a diffusion proportional to $\sin(\theta_n)$, based on an angle of divergence $\alpha(=\theta_n)$ between the emission reference line Ref extending perpendicular to the scan axis (Z-axis) from the center of the beam of X-ray tube R and a projection line extending from the X-ray tube R to the row of pixels i. An appropriate low-pass filter is applied to reduce artifacts that would appear in a position in the more pronounced way, the farther away along the scan axis that position is from a center plane located substantially centrally of the region of interest of patient M and extending perpendicular to the scan axis. Thus, artifacts are suppressed from appearing in positions of a reconstructed image remote along the scan axis (Z-axis).

In the above embodiment, a low-pass filtering is carried out on each row of pixels of projection data detected by the flat panel X-ray detector D as a diffusion proportional to $\sin(\theta n)$. Instead, a diffusion proportional to $\sin(\theta_n)$ on the flat panel X-ray detector D may be carried out as follows. The gate lines of the flat panel detector D may be arranged in a direction corresponding to the direction along the scan axis (Z-axis). By simultaneously turning on the gates of a predetermined number of rows of pixels corresponding to the direction along the scan axis (Z-axis), signals of a plurality of pixels for the predetermined number of the rows of pixels are read simultaneously, thereby obtaining a summed signal. In this way, a diffusion proportional to $\sin(\theta_n)$ on the area detector (flat panel X-ray detector D) may be carried out. This is equivalent to the application of the low-pass filter noted above. Thus, data collection with the low-pass filter applied to the predetermined number of the rows of pixels may be achieved in the form of hardware by controlling the area detector (flat panel X-ray detector D) to read the data of the predetermined number of the rows of pixels simultaneously.

The above embodiment is applicable also to a cone beam CT in which the X-ray tube R and flat panel X-ray detector D are continuously revolved, e.g. in a helical scan.

This invention is not limited to the foregoing embodiment, but may be modified as follows:

(1) In the above embodiment, the driver 30 synchronously drives the X-ray tube R and flat panel X-ray detector D opposed to each other across the patient M, to make one revolution (at least a half revolution) in the same plane about the scan axis (Z-axis) set substantially centrally of the region of interest of patient M. In this way, a CT type X-ray radiography is performed. Instead, other scan modes may be employed as described hereunder to perform a non-CT type X-ray radiography (in which the X-ray tube R and flat panel X-ray detector D are not caused to make more than a half revolution about the body axis of the patient).

Figure 13A:
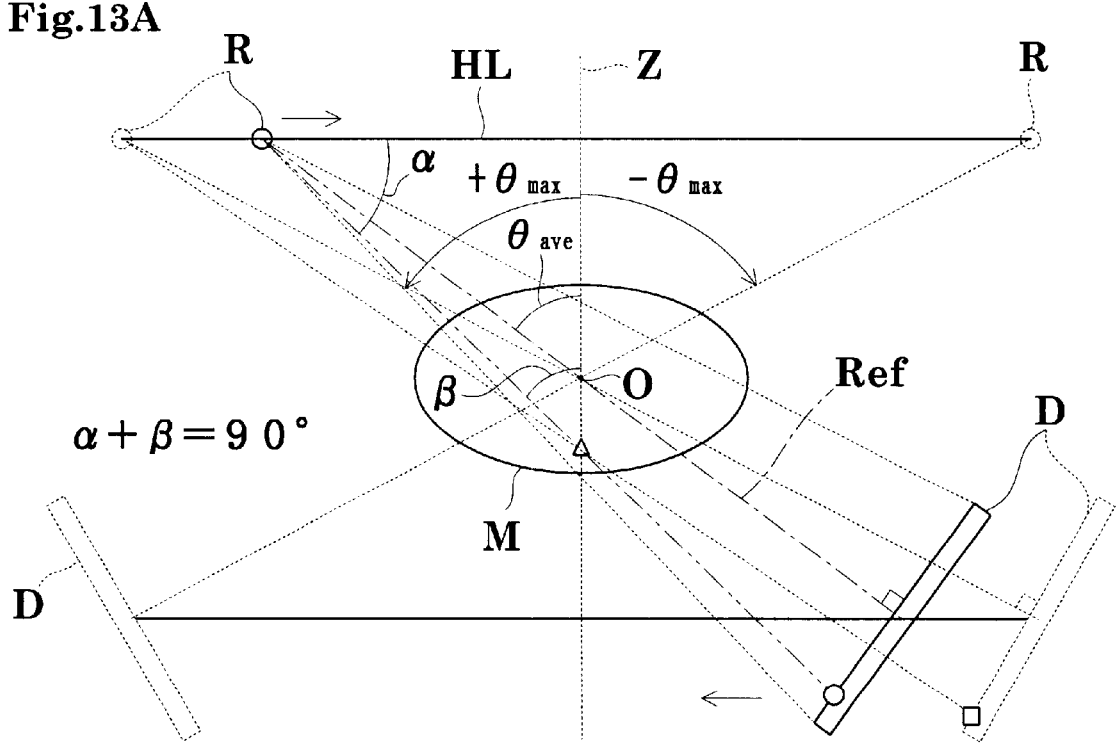
FIGS. 13A and 13B are views showing other image pickup modes of a non-CT type X-ray radiographic apparatus.

As shown in FIG. 13A, for example, the driver 30 may drive the X-ray tube R and flat panel X-ray detector D to move linearly and parallel to each other with the patient M lying in between, with one of the X-ray tube R and flat panel X-ray detector D movable in a first direction, and the other movable in a second direction counter to the first direction. Thus, by causing the X-ray tube R and flat panel X-ray detector D to move linearly, parallel to each other, and scan the patient M lying in between, a non-CT type radiography may be carried out to enable an image reconstruction to generate three-dimensional volume data of a region of interest of patient M. In the case of this linear scanning, as shown in FIG. 13A, an angle between the center of the cone beam from the X-ray tube R and the Z-axis which is a scan axis changes with each scan position, i.e. changes within a range of +θmax to −θmax. With this in view, an average angle θave is determined, for example, by computing a root-mean-square of angles in predetermined scan positions between the Z-axis and the center of the cone beam from the X-ray tube R. Then, projection data in each row of pixels of flat panel X-ray detector D is subjected to a low-pass filtering as a diffusion proportional to $\sin(\alpha)$, where a is an angle formed between a horizontal (straight line) HL perpendicular to the Z-axis and each row of pixels of flat panel X-ray detector D when the angle between the Z-axis and the center of the cone beam from the X-ray tube R coincides with the average angle θave. This operation effectively reduces artifacts due to missing cones variable in size with an angle of divergence (90°−|θ|). As shown in FIG. 13A, the same low-pass filtering corresponding to α is applied, for example, to the projection data in a row of pixels indicated by a circle of flat panel X-ray detector D from a certain scan position and to the projection data in a row of pixels indicated by a square (different from the row of pixels indicated by the circle) of flat panel X-ray detector D from a different scan position.

Figure 13B:
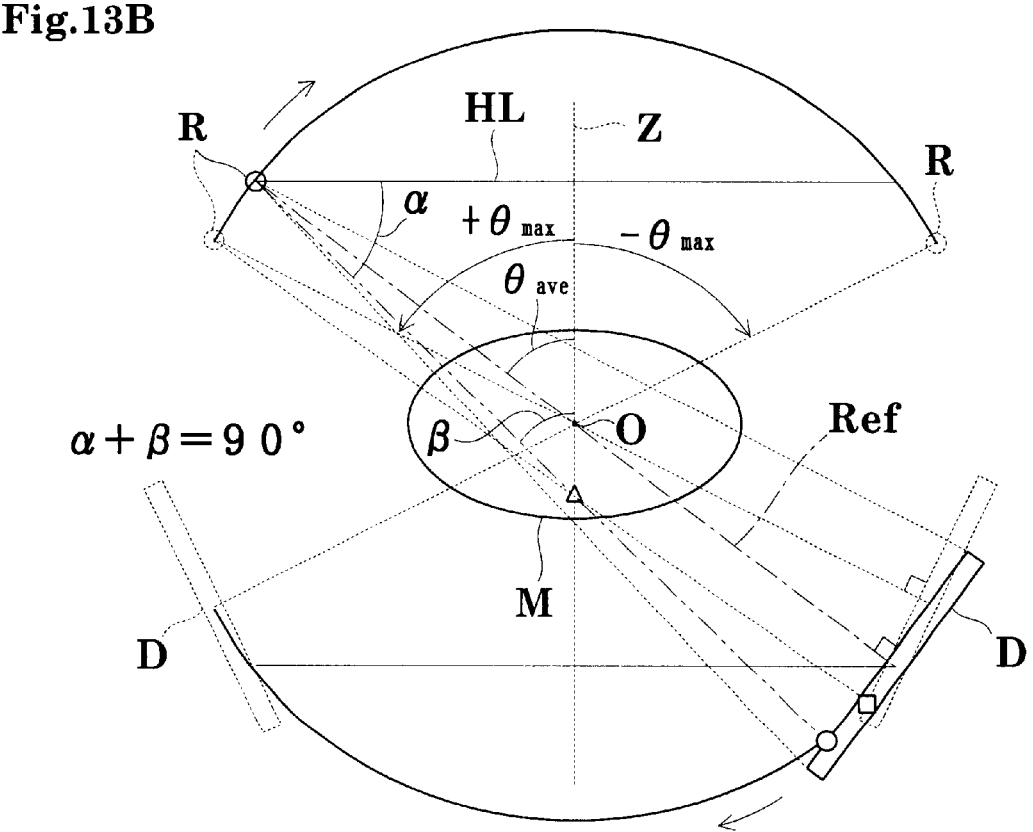

As shown in FIG. 13B, two arcuate tracks may be set on a circumferential track around the patient M to be opposed to each other across the patient M, and the driver 30 may drive the X-ray tube R to move on one of the arcuate tracks, and the flat panel X-ray detector D to move on the other arcuate track in synchronism therewith to maintain a fixed distance from the X-ray tube R, to perform what is known as arcuate scanning. Thus, by causing the X-ray tube R and flat panel X-ray detector D to move separately and arcuately and scan the patient M lying in between, a non-CT type radiography may be carried out to enable an image reconstruction to generate three-dimensional volume data of a region of interest of patient M. In the case of this arcuate scanning, as shown in FIG. 13B, an angle between the center of the cone beam from the X-ray tube R and the Z-axis which is a scan axis changes with each scan position, i.e. changes within a range of +θmax to −θmax. With this in view, an average angle θave is determined, for example, by computing a root-mean-square of angles in predetermined scan positions between the Z-axis and the center of the cone beam from the X-ray tube R. Then, projection data in each row of pixels of flat panel X-ray detector D is subjected to a low-pass filtering as a diffusion proportional to $\sin(\alpha)$, where a is an angle formed between a horizontal (straight line) HL perpendicular to the Z-axis and each row of pixels of flat panel X-ray detector D when the angle between the Z-axis and the center of the cone beam from the X-ray tube R coincides with the average angle θave. This operation effectively reduces artifacts due to missing cones variable in size with an angle of divergence (90°−|θ|). As shown in FIG. 13B, the same low-pass filtering corresponding to a is applied, for example, to the projection data in a row of pixels indicated by a circle of flat panel X-ray detector D from a certain scan position and to the projection data in a row of pixels indicated by a square (different from the row of pixels indicated by the circle) of flat panel X-ray detector D from a different scan position.

In the non-CT type radiography based on the linear scanning and arcuate scanning, projection data in each row of pixels of flat panel X-ray detector D may be subjected to a low-pass filtering to pass the lower frequency in positions on the Z-axis the closer to the X-ray tube R.

Figure 14:
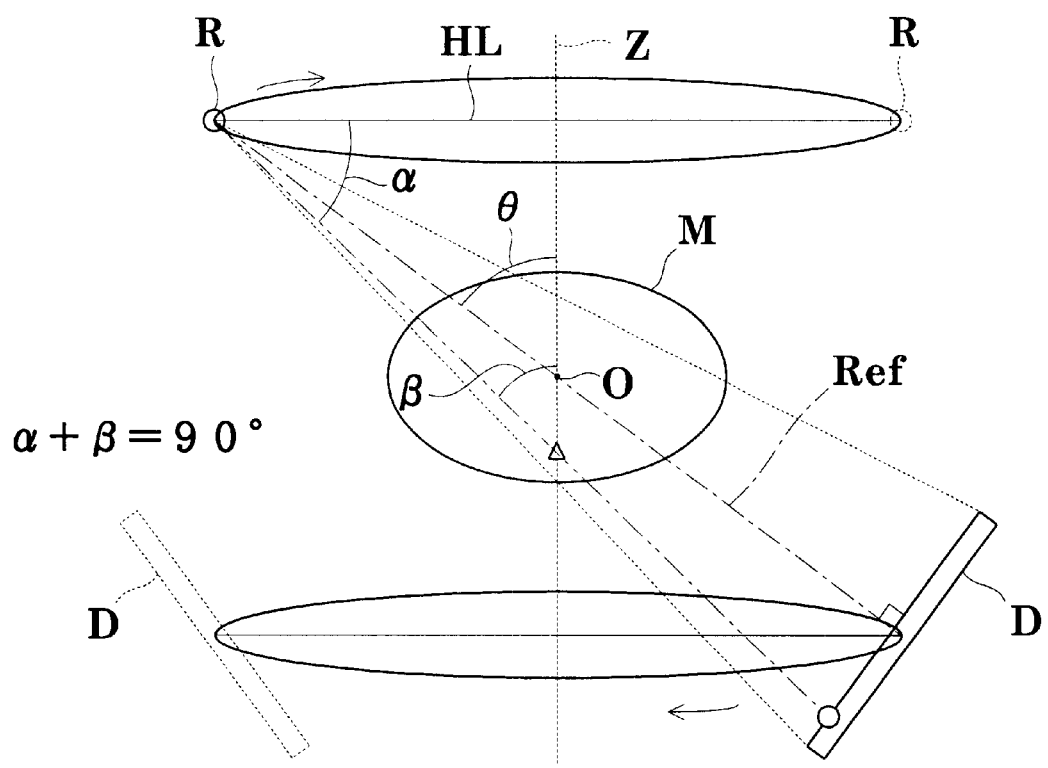
FIG. 14 is a view showing an image pickup mode of a non-CT type X-ray radiographic apparatus.

As shown in FIG. 14, the driver 30 may drive the X-ray tube R to revolve in one of parallel planes opposed to each other across the patient M, and the flat panel X-ray detector D to revolve in the other plane in synchronism therewith in a direction counter to the direction of revolution of X-ray tube R, to perform what is known as circular scanning. Thus, by causing the X-ray tube R and flat panel X-ray detector D to revolve separately in the two parallel planes opposed to each other across the patient M, a non-CT type radiography may be carried out to enable an image reconstruction to generate three-dimensional volume data of a region of interest of patient M. In the case of this circular scanning, as shown in FIG. 14, projection data in each row of pixels of flat panel X-ray detector D is subjected to a low-pass filtering as a diffusion proportional to $\sin(\alpha)$, where $\alpha$ is an angle formed between a horizontal (straight line) HL perpendicular to the Z-axis which is the scan axis and each row of pixels of flat panel X-ray detector D. This operation effectively reduces artifacts due to missing cones variable in size with an angle of divergence $\alpha$.

In the non-CT type radiography based on the circular scanning, projection data in each row of pixels of flat panel X-ray detector D may be subjected to a low-pass filtering to pass the lower frequency, the smaller the angle $\alpha$ is.

In the non-CT type radiographic apparatus shown in FIGS. 13 and 14, the X-ray tube R and flat panel X-ray detector D are opposed to each other, such that the center point of X rays emitted in the form of a cone beam from the X-ray tube R always passes through the center point O of a particular sectional plane of patient M, and impinges on the center point of the detecting plane of flat panel X-ray detector D in a direction perpendicular thereto. The detecting plane of flat panel X-ray detector D may be maintained parallel to the sectional planes of patient M.

Though the X-ray tube R and flat panel X-ray detector D are moved in scanning action, the X-ray tube R may be fixed, with the flat panel X-ray detector D and patient M movable during the scanning, for example. Alternatively, the flat panel X-ray detector D may be fixed, with the X-ray tube R and patient M movable during the scanning. Thus, scanning may be performed by moving any two of the X-ray tube R, flat panel X-ray detector D and patient M.

(2) The convolution unit 54 in the foregoing embodiment carries out a low-pass filtering after an $|\omega|$ filtering, but whichever may be carried out first. In the foregoing embodiment, both the $|\omega|$ filtering and low-pass filtering are carried out in the Fourier space, but both may be carried out in the real space. One may be carried out in the real space and the other in the Fourier space. The foregoing embodiment employs the Gaussan filter function as one example of filter functions for the low-pass filtering. A different filter function may be employed such as a sine wave filter function.

(3) The convolution unit 54 in the foregoing embodiment carries out the low-pass filtering as a diffusion proportional to $\sin(\theta_n)$ on each row of pixels of projection data detected by the flat panel X-ray detector D. The convolution unit 54 may apply a low-pass filtering to pass the lower frequency for the projection data in the row of pixels i of flat panel X-ray detector D the farther away from the emission reference line Ref extending perpendicular to the scan axis (Z-axis) from the center of the beam of X-ray tube R as shown in FIG. 10.

Figure 15A:
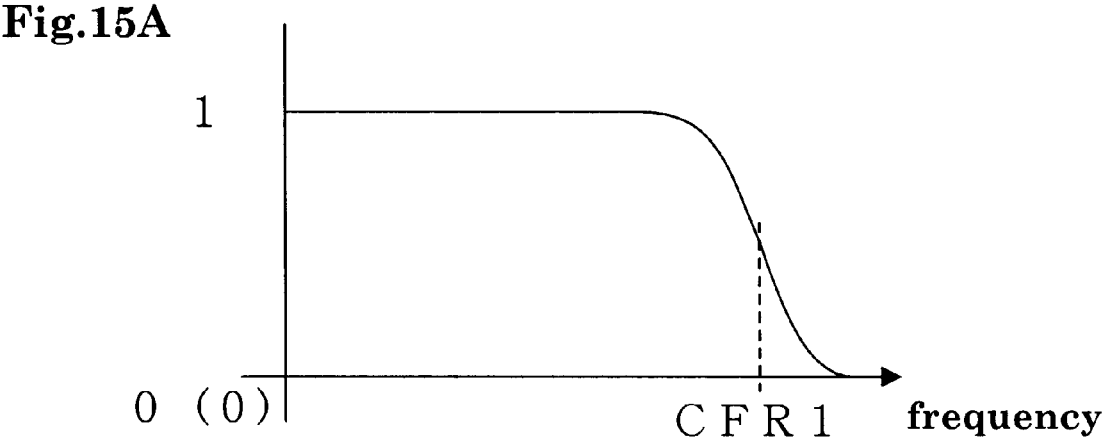
FIGS. 15A through 15C are characteristic views showing low-pass filter characteristics in which the lower frequency is passed for the row of pixels on the flat panel X-ray detector farther way from an emission reference line.
Figure 15B:
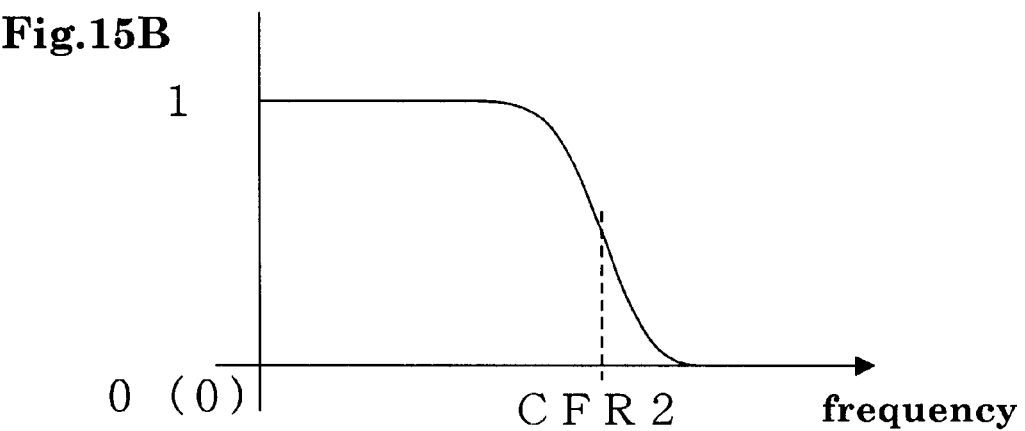
Figure 15C:
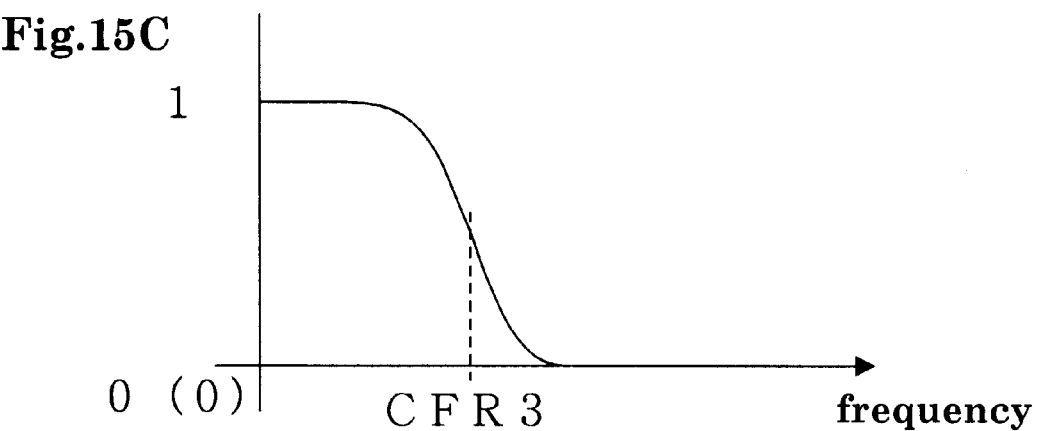

Specifically, as shown in FIG. 15A, a low-pass filtering (e.g. at a cutoff frequency CFR1) is applied to the projection data in a row of pixels i of flat panel X-ray detector D close to the emission reference line Ref. Thus, high frequency components are hardly cut, and the components from direct current to cutoff frequency CFR1 are passed. Next, as shown in FIG. 15B, a low-pass filtering (e.g. at a cutoff frequency CFR2) is applied to the projection data in a row of pixels i of flat panel X-ray detector D farther away from the emission reference line Ref, to pass the components from direct current to cutoff frequency CFR2. Next, as shown in FIG. 15C, a low-pass filtering (e.g. at a cutoff frequency CFR3) is applied to the projection data in a row of pixels i of flat panel X-ray detector D still farther away from the emission reference line Ref, to pass the components from direct current to cutoff frequency CFR3. These cutoff frequencies are in a relationship CFR3<CFR2<CFR1. In this way, the low-pass filtering is applied to pass the lower frequency for the projection data in the rows of pixels i of flat panel X-ray detector D the farther away from the emission reference line Ref. In this case also, appropriate low-pass filters are applied to reduce artifacts that would appear in a position in the more pronounced way, the farther away along the scan axis (Z-axis) that position is from a center plane located substantially centrally of the region of interest of patient M and extending perpendicular to the scan axis (Z-axis). Thus, artifacts are suppressed from appearing in positions of a reconstructed image remote along the scan axis (Z-axis).

(4) In the foregoing embodiment, the flat panel X-ray detector D is employed as the area detector. Various other two-dimensional area detectors may be employed, such as an image intensifier tube and an imaging plate.

(5) The radiographic apparatus in the foregoing embodiment is used for medical purposes in radiographing patient M. Such radiographic apparatus may be adapted for use in nondestructive testing, for example, of various electronic parts such as BGA (Ball Grid Array) substrates, printed circuit boards and so on.

(6) In the foregoing embodiment, the patient M is irradiated with X rays emitted from the X-ray tube R. Instead of X rays, other penetrating types of electromagnetic waves such as gamma rays and light may be used to produce similar effects. Thus, the radiographic apparatus according to this invention is not limited to X-ray radiographic apparatus. The invention is applicable also to radiographic apparatus for performing radiography by using the types of electromagnetic waves other than X rays that penetrate objects under examination.

This invention may be embodied in other specific forms without departing from the spirit or essential attributes thereof and, accordingly, reference should be made to the appended claims, rather than to the foregoing specification, as indicating the scope of the invention.

What is claimed is:

1. A radiographic apparatus for obtaining sectional images from three-dimensional volume data of a region of interest of an object under examination generated by an image reconstruction of projection data acquired by radiographing the object from varied scan positions, said apparatus comprising:

a radiation source for irradiating said object with penetrating electromagnetic waves in form of a divergent beam;

an area detector opposed to said radiation source across said object for detecting electromagnetic waves transmitted through said object;

scanning means for causing said radiation source and said area detector synchronously to revolve in an identical plane about a scan axis set substantially centrally of said region of interest;

an image processor for performing a predetermined image processing on projection data detected in the varied scan positions; and a back projection unit for performing the image reconstruction to generate three-dimensional volume data of the region of interest by projecting the projection data processed by said image processor back to predetermined lattice points of a three-dimensional lattice virtually set to the region of interest of the object radiographed;

said image processor applying a low-pass filtering to projection data in each row of pixels of said area detector perpendicular to a direction corresponding to said scan axis, said low-pass filtering being in accordance with a location on said scan axis to which said each row of pixels is projected.

2. A radiographic apparatus as defined in claim 1, wherein said image processor is arranged to apply a low-pass filtering to pass the lower frequency for projection data in a row of pixels of said area detector the farther away from an emission reference line extending perpendicular to said scan axis from a beam center of said radiation source.

3. A radiographic apparatus as defined in claim 1, wherein said image processor is arranged to apply a low-pass filtering as a diffusion proportional to $\sin(\alpha)$, where $\alpha$ is an angle of divergence formed between an emission reference line extending perpendicular to said scan axis from a beam center of said radiation source and a projection line extending from said radiation source and each row of pixels of said area detector.

4. A radiographic apparatus as defined in claim 1, wherein said area detector is a flat panel detector with gate lines arranged in a direction corresponding to a direction of said scan axis, said image processor applying the low-pass filtering by simultaneously turning on gates of a predetermined number of rows of pixels corresponding to the direction of said scan axis.

5. A radiographic apparatus as defined in claim 1, wherein said scanning means performs, instead of said scanning by revolution in the identical plane, a linear scanning for linearly moving one of said radiation source and said area detector in a first direction perpendicular to said scan axis, and the other synchronously therewith in a second direction parallel and counter to said first direction.

6. A radiographic apparatus as defined in claim 1, wherein two arcuate tracks are set on a circumferential track around the object to be opposed to each other across the object such that a straight line between midpoints of the two arcuate tracks coincides with said scan axis, said scanning means performing, instead of said scanning by revolution in the identical plane, an arcuate scanning for moving said radiation source on one of the arcuate tracks, and said area detector on the other arcuate track synchronously therewith to maintain a fixed distance from said radiation source.

7. A radiographic apparatus as defined in claim 1, wherein said scanning means performs, instead of said scanning by revolution in the identical plane, a circular scanning for revolving said radiation source in one of parallel planes opposed to each other across the object and extending perpendicular to said scan axis, and said area detector in the other plane synchronously therewith and in a direction opposite to a direction of revolution of said radiation source.

8. A radiographic apparatus as defined in claim 5, wherein said image processor applies the low-pass filtering to pass the lower frequency in positions on said scan axis the closer to said radiation source.

9. A radiographic apparatus as defined in claim 6, wherein said image processor applies the low-pass filtering to pass the lower frequency in positions on said scan axis the closer to said radiation source.

10. A radiographic apparatus as defined in claim 7, wherein said image processor applies the low-pass filtering to projection data in each row of pixels of said area detector to pass the lower frequency the smaller an angle $\alpha$ is, the angle $\alpha$ being between said parallel planes and each row of pixels of said area detector.

11. A radiographic apparatus as defined in claim 5, wherein said image processor applies the low-pass filtering to projection data in each row of pixels of said area detector as a diffusion proportional to $\sin(\alpha)$, where $\alpha$ is an angle formed between said first direction and each row of pixels of said area detector when an angle between said scan axis and a beam center of said radiation source coincides with an average angle derived from angles between said scan axis and the beam center of said radiation source in predetermined scan positions.

12. A radiographic apparatus as defined in claim 6, wherein said image processor applies the low-pass filtering to projection data in each row of pixels of said area detector as a diffusion proportional to $\sin(\alpha)$, where $\alpha$ is an angle formed between said scan axis and each row of pixels of said area detector when an angle between said scan axis and a beam center of said radiation source coincides with an average angle derived from angles between said scan axis and the beam center of said radiation source in predetermined scan positions.

13. A radiographic apparatus as defined in claim 7, wherein said image processor applies the low-pass filtering to projection data in each row of pixels of said area detector as a diffusion proportional to $\sin(\alpha)$, where $\alpha$ is an angle between said parallel planes and each row of pixels of said area detector.

14. A radiographic apparatus as defined in claim 4, wherein said scanning means performs, instead of said scanning by revolution in the identical plane, a linear scanning for linearly moving one of said radiation source and said area detector in a first direction, and the other synchronously therewith in a second direction parallel and counter to said first direction.

15. A radiographic apparatus as defined in claim 4, wherein two arcuate tracks are set on a circumferential track around the object to be opposed to each other across the object, said scanning means performing, instead of said scanning by revolution in the identical plane, an arcuate scanning for moving said radiation source on one of the arcuate tracks, and said area detector on the other arcuate track synchronously therewith to maintain a fixed distance from said radiation source.

16. A radiographic apparatus as defined in claim 4, wherein said scanning means performs, instead of said scanning by revolution in the identical plane, a circular scanning for revolving said radiation source in one of parallel planes opposed to each other across the object, and said area detector in the other plane synchronously therewith and in a direction opposite to a direction of revolution of said radiation source.

* * * * *